(12) United States Patent
Singbartl et al.

(10) Patent No.: US 9,057,722 B2
(45) Date of Patent: *Jun. 16, 2015

(54) URINARY BIOMARKERS FOR PREDICTING LONG-TERM DIALYSIS

(71) Applicant: University of Pittsburgh—Of The Commonwealth System Of Higher Education, Pittsburgh, PA (US)

(72) Inventors: Kai Singbartl, Pittsburgh, PA (US); John A. Kellum, Pittsburgh, PA (US)

(73) Assignee: University of Pittsburgh—of the Commonwealth System of Higher Education, Pittsburgh, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/331,694

(22) Filed: Jul. 15, 2014

(65) Prior Publication Data
US 2014/0329256 A1 Nov. 6, 2014

Related U.S. Application Data

(63) Continuation of application No. 13/945,477, filed on Jul. 18, 2013, now Pat. No. 8,815,602, which is a continuation of application No. 12/565,483, filed on Sep. 23, 2009, now Pat. No. 8,501,489.

(60) Provisional application No. 61/100,588, filed on Sep. 26, 2008.

(51) Int. Cl.
| G01N 33/543 | (2006.01) |
| G01N 33/00 | (2006.01) |
| G01N 33/53 | (2006.01) |
| A61M 1/14 | (2006.01) |

(52) U.S. Cl.
CPC ... *G01N 33/5308* (2013.01); *Y10T 436/142222* (2015.01); *Y10T 436/143333* (2015.01); *Y10T 436/14* (2015.01); *Y10T 436/00* (2015.01); *G01N 2400/40* (2013.01); *G01N 2800/347* (2013.01); *A61M 1/14* (2013.01); *G01N 33/543* (2013.01)

(58) Field of Classification Search
CPC .... G01N 33/543; G01N 33/00; Y10T 436/00; Y10T 436/11; Y10T 436/21; Y10T 436/212
USPC .................. 436/94, 93, 91
See application file for complete search history.

(56) References Cited

U.S. PATENT DOCUMENTS

| 6,350,571 B1 | 2/2002 | Lokeshwar et al. ........... 435/4 |
| 2005/0158801 A1 | 7/2005 | Hu et al. ........... 435/7.2 |

FOREIGN PATENT DOCUMENTS

| CN | 1867902 A | 11/2006 |
| JP | H10339730 A | 12/1998 |
| JP | 2000504114 A | 4/2000 |

OTHER PUBLICATIONS

Herrera et al. "Exogenous mesenchymal stem cells localize to the kidney by means of CD44 following acute tubular injury". 2007. Kidney International. vol. 72. pp. 430-441.*
Lipkin et al. "Hyaluronic acid metabolism and its clinical significance in patients treated by continuous ambulatory peritoneal dialysis." 1993. Nephrol. Dial. Transpl. vol. 8, pp. 357-360.*
Bitter and Muir, "A Modified Uronic Acid Carbazole Reaction." *Anal. Biochem.*, 4:330-334 (1962).
Csoka, et al., "Hyaluronidases in Tissue Invasion." *Invasion Metastasis*, 17:297-311 (1997).
Delpech, et al., "Hyaluronan: Fundamental Principles and Applications in Cancer." *J Intern Med.*, 242:41-48 (1997).
Dygert, et al., "Determination of Reducing Sugars With Improved Precision." *Anal. Biochem.*, 13:367-374 (1965).
Fosang, et al., "An ELISA Plate-Based Assay for Hyaluronan Using Biotinylated Proteoglycan G1 Domain (HA-Binding Region)." *Matrix*, 10:306-313 (1990).
Fraser and Laurent, "Turnover and Metabolism of Hyaluronan." in: *Biology of Hyaluronan*, (J. Whelan, ed.), pp. 41-59, New York, Wiley Chichister (Ciba Foundation Symposium 143) (1989).
Gold, "Purification and Properties of Hyaluronidase From Human Liver." *Biochem. J.*, 205:69-74 (1982).
Hobarth, et al., "Topical Chemo-Prophylaxis of Superficial Bladder Cancer by Mitomycin C and Adjuvant Hyaluronidase." *Eur. Urol.*, 21:206-210 (1992).
Knudson, et al., "The Role and Regulation of Tumor-Associated Hyaluronan." In: *The Biology of Hyaluronan*, (J. Whelan, ed.) pp. 150-169, New York, Wiley, Chichester (Ciba Foundation Symposium 143) (1989).
Laurent, et al., "Hyaluronan." *FASEB J.*, 6:2397-2404 (1992).
Lin, et al., "A Hyaluronidase Activity of the Sperm Plasma Membrane Protein PH-20 Enables Sperm to Penetrate the Cumulus Layer Surrounding the Egg." *J. Cell Biol.*, 125:1157-1163 (1995A).
Lin, et al., "Urinary Hyaluronic Acid Is a Wilms' Tumor Marker." *J. Ped. Surg.*, 30:304-308 (1995B).

(Continued)

*Primary Examiner* — Christine T Mui
(74) *Attorney, Agent, or Firm* — Medlen & Carroll, LLP (57) ABSTRACT

This invention is related to the field of the prevention and treatment of kidney disease. The treatment of kidney disease may be tailored depending upon the need for, or expectation of, long-term dialysis. For example, prediction of long-term dialysis treatment can be determined by monitoring urine biomarkers related to the development of chronic kidney disease. For example, a normalized time course of hyaluronic acid can be used to determine whether a patient having suffered acute kidney injury will require long-term dialysis.

9 Claims, 6 Drawing Sheets

(56) References Cited

OTHER PUBLICATIONS

Lokeshwar, et al., "Ankyrin Binding Domain of CD44(GP85) Is Required for the Expression of Hyaluronic Acid-Mediated Adhesion Function." *J. Cell Biol.*, 126:1099-1109 (1994).

Lokeshwar, et al., "Differences in Hyaluronic Acid Mediated Functions and Signaling in Arterial, Microvessel, and Vein-Derived Human Endothelial Cells." *J Biol Chem.*, 275:27641-27649 (2000A).

Lokeshwar, et al., "Urinary Hyaluronic Acid and Hyaluronidase: Markers for Bladder Cancer Detection and Evaluation of Grade." *J Urol.*, 163:348-356 (2000B).

Lokeshwar, et al., "Bladder Tumor Markers for Monitoring Recurrence and Screening Comparison of Hyaluronic Acid-Hyaluronidase and BTA-Stat Tests." *Cancer*, 95:61-72 (2002).

McCormick and Zetter, "Adhesive Interactions in Angiogenesis and Metastasis." *Pharmacol. Ther.*, 53:239-260 (1992).

Pecoits-Filho, et al., "Associations Between Circulating Inflammatory Markers and Residual Renal Function in CRF Patients." *Am J Kidney Dis.*, 41(6):1212-8 (2003).

Roden, et al., "Enzymatic Pathways of Hyaluronan Catabolism." *In: The Biology of Hyaluronan*, (J. Whelan, ed.), pp. 60-86, New York, Wiley Chichister (Ciba Foundation Symposium 143) (1989).

Sattar, et al., "Does Hyaluronan Have a Role in Endothelial Cell Proliferation of the Synovium?" *Semin Arthritis Rheum;* 22:37-43 (1992).

Stern, et al., "Hyaluronidase Levels in Urine From Wilms' Tumor Patients." *J. Natl. Canc. Inst.*, 83:1569-1574 (1991).

Tengblad, "Affinity Chromatography on Immobilized Hyaluronate and Its Application to the Isolation of Hyaluronate Binding Properties From Cartilage." *Biochim. Biophys. Acta,* 578:281-289 (1979).

West, et al., "Angiogenesis Induced by Degradation Products of Hyaluronic Acid." *Science,* 228:1324-1326 (1985).

Zhu, et al., "Molecular Cloning of a Mammalian Hyaluronidase Reveals Identity With Hemopexin, A Serum Heme-Binding Protein." *J. Biol. Chem.,* 269:32092-32097 (1994).

Supplementary ESR dated Jan. 4, 2013.

Erickson, et al., "Increased Urinary Hyaluronic Acid and Interstitial Cystitis." *The Journal of Urology,* 160(4):1282-1284 (1998).

Göransson, et al., "Renal hyaluronan accumulation and hyaluronan synthase expression after ischaemia-reperfusion injury in the rat." *Nephrology Dialysis Transplantation,* 19(4):823-830 (2004).

Stenvinkel, et al., "High serum hyaluronan indicates poor survival in renal replacement therapy." *American Journal of Kidney Diseases,* 34(6):1083-1088 (1999).

Wells, et al., "Increased Hyaluronan in Acutely Rejecting Human Kidney Grafts." *Transplantation,* 55(6):1346-1348 (1993).

Herrera, et al., "Exogenous mesenchymal stem cells localize to the kidney by means of CD44 following acute tubular injury." *Kidney International.,* 72:430-441 (2007).

Lipkin, et al., "Hyaluronic acid metabolism and its clinical significance in patients treated by continuous ambulatory peritoneal dialysis." *Nephrol. Dial. Transpl.,* 8:357-360 (1993).

Levey, et al., "Definition and classification of chronic kidney disease: A position statement from Kidney Disease: Improving Global Outcomes (KDIGO)." *Kidney International.,* 67:2089-2100 (2005).

Bellomo et al., "Acute renal failure—definition, outcome measures, animal models, fluid therapy and information technology needs: the Second International Consensus Conference of the Acute Dialysis Quality Initiative (ADQI) Group." *Critical Care* 8(4):R204-R212 (Epub 2004).

Girard, et al., "Characterization of hyaluronic acid on tissue sections with hyalurectin." *Histochem Cytochem.,* 34:539-541 (1986).

Turney, et al., "Hyaluronic Acid in End-Stage Renal Failure Treated by Haemodialysis: Clinical Correlates and Implications." *Nephrol Dial Transplant* 6: 566-570 (1991).

Lu Lan, "Clinical Significances of Determinations of Hyaluronic acid, Procollagen III, Collagen IV and Laminin in the serum of a nephrotic patient." *Journal of Guangxi Medical University,* 19(5):655-656,Chinese (2002).

Lu Lan, "Clinical Significances of Determinations of Hyaluronic acid, Procollagen III, Collagen IV and Laminin in the serum of a nephrotic patient." *Journal of Guangxi Medical University,* 19(5):655-656,English Translation (2002).

Harward and Falk, "The Kidney Care Prevention Program: an innovative approach to chronic kidney disease prevention" *N C Med J.* 69(3):233-6 (2008).

Fraser, et al., "Plasma clearance, tissue distribution and metabolism of hyaluronic acid injected intravenously in the rabbit." *Biochem. J.,* 415-424 (1981).

Herrero-Morín, et al., "Cystatin C and beta2-microglobulin: markers of glomerular filtration in critically ill children." *Critical Care,* 11:R59:1-7 (2007).

Safirstein, et al., "Reduced renal prepro-epidermal growth factor mRNA and decreased EGF excretion in ARF." *Kidney International,* 36:810-815 (1989).

\* cited by examiner

URINARY BIOMARKERS FOR PREDICTING LONG-TERM DIALYSIS

STATEMENT OF GOVERNMENTAL SUPPORT

This invention was made with government support awarded by the National Institutes of Diabetes And Digestive And Kidney Diseases (grant number 5R01DK070910-03). The government has certain rights in the invention.

FIELD OF INVENTION

This invention is related to the field of the prevention and treatment of kidney disease. The treatment of kidney disease may be tailored depending upon the need for, or expectation of, long-term dialysis. For example, prediction of long-term dialysis treatment can be determined by monitoring urine biomarkers related to the development of chronic kidney disease. For example, a normalized time course of hyaluronic acid can be used to determine whether a patient having suffered acute kidney injury will require long-term dialysis.

BACKGROUND

Chronic kidney disease (CKD) is believed to be one of the biggest and fastest growing health concerns facing the developed world. In the US alone, 26 million people have CKD and another 20 million more are at increased risk. CKD leads to dialysis and heart disease and costs billions of dollar. A major cause of CKD is acute kidney injury (AKI), which is itself an independent predictor of morbidity and mortality and is associated with substantially increased healthcare costs, especially if dialysis (or a related kidney support technique) is required.

Chronic kidney disease can develop as a result of many different factors, but most notably, genetic predisposition and/or acute kidney injury. The degree of kidney injury is also associated with an incremental increase in long-term mortality. Crude 1-yr case-fatality after hospital discharge can be as high as 64% for patients with severe, dialysis-requiring AKI. Moreover, currently used markers of kidney function/injury, such as serum creatinine levels, are poor at discriminating long-term outcome of kidney disease. Regardless of the initiating factor, chronic kidney disease has a high proportion of patients requiring long-term dialysis (i.e., for example, renal replacement therapy or RRT). This treatment is expensive, time consuming, and can be untoward side effects, including, but not limited to, blood vessel stenosis and/or thromobosis.

Thus, development of a biomarker that allows early identification and subsequent stratification of patients with AM and also predicts recovery of kidney function, is a clinical tool having great need in the art.

SUMMARY

This invention is related to the field of the prevention and treatment of kidney disease. The treatment of kidney disease may be tailored depending upon the need for, or expectation of, long-term dialysis. For example, prediction of long-term dialysis treatment can be determined by monitoring urine biomarkers related to the development of chronic kidney disease. For example, a normalized time course of hyaluronic acid can be used to determine whether a patient having suffered acute kidney injury will require long-term dialysis.

In one embodiment, the present invention contemplates a method, comprising a) providing; i) a patient, wherein the patient exhibits an acute kidney injury; ii) at least two urine samples derived from the patient; b) detecting persistently elevated hyaluronic acid in the urine samples; c) predicting the patient to require long-term dialysis. In one embodiment, wherein the samples are collected on the first and fourteenth day after initiation of replacement therapy for severe kidney injury. In one embodiment, the method further comprises diagnosing the patient with chronic kidney disease. In one embodiment, the diagnosing occurs at least sixty days after the kidney injury. In one embodiment, the method further comprises entering the patient in a chronic kidney disease prevention program.

In one embodiment, the present invention contemplates a method, comprising a) providing; i) a patient, wherein the patient exhibits an acute kidney injury, wherein the patient is at risk for development of chronic kidney disease; ii) at least two urine samples derived from the patient; b) detecting persistently elevated hyaluronic acid in the urine samples; c) treating the patient to prevent chronic kidney disease. In one embodiment, the treating is initiated on day 14 after the kidney disease.

In one embodiment, the present invention contemplates a method comprising: a) providing; i) a patient having suffered an acute kidney injury; ii) obtaining a plurality of urinary hyaluronic acid and creatinine levels from the patient, wherein the levels are obtained over time; b) constructing a urinary hyaluronic acid level time course, wherein the time course is normalized against the urinary creatinine levels; and c) predicting chronic kidney disease development. In one embodiment, wherein the predicting includes long-term renal replacement therapy (i.e., for example, dialysis).

DEFINITIONS

The term "biomarker" as used herein, refers to any biological compound related to the progressive development of chronic kidney disease. For example, a biomarker may comprise hyaluronic acid, or any of its metabolites or derivatives.

The term "prognosis" as used herein, refers to a medical conclusion based upon an analysis any biomarker that provides information regarding the progression of medical conditions including, but not limited to, chronic kidney disease or cardiovascular disease. Such information includes, but is not limited to the determination of a long-term dialysis risk.

The term "predicting" as used herein, refers to a method of forming a prognosis, wherein a medically trained person analyzes biomarker information.

The term "chronic kidney disease" as used herein, refers to a medical condition wherein exemplary symptoms may include, but are not limited to, hyperphosphatemia (i.e., for example, >4.6 mg/dl) or low glomerular filtration rates (i.e., for example, <90 ml/minute per 1.73 $m^2$ of body surface). However, many CKD patients may have normal serum phosphate levels in conjunction with a sustained reduction in glomerular filtration rate for 3 or more months, or a normal GFR in conjunction with sustained evidence of a structural abnormality of the kidney. In some cases, patients diagnosed with chronic kidney disease are placed on hemodialysis to maintain normal blood homeostasis (i.e., for example, urea or phosphate levels). Alternatively, "chronic kidney disease" refers to a medical condition wherein a patients has either i) a sustained reduction in GFR <60 ml/min per 1.73 $m^2$ of body surface for 3 or more months; or ii) a structural or functional abnormality of renal function for 3 or more months even in the absence of a reduced GFR. Structural or anatomical abnormalities of the kidney could be defined as but not limited to persistent microalbuminuria or proteinuria or hematuria or presence of renal cysts.

The term "asymptomatic" as used herein, refers to a patient and/or subject that does not have CKD, wherein a CKD symptom includes having a reduced glomerular filtration rate (i.e., for example, between approximately 70-89 ml/min per 1.73 $m^2$ of body surface) for less than three months.

The term "glomerular filtration rate" as used herein, refers to a measurement capable of determining kidney function (infra). In general, normal glomerular filtration rates range between approximately 120-90 ml/minute per 1.73 m2 of body surface. Compromised kidney function is assumed when glomerular filtration rates are less than 90 ml/minute per 1.73 m2 of body surface. Kidney failure is probable when glomerular filtration rates fall below approximately 30 ml/minute per 1.73 m2 of body surface. Dialysis is frequently initiated when glomerular filtration rates fall below approximately 15 ml/minute per 1.73 m2 of body surface.

The term "renal failure" as used herein, refers to any acute (sudden) or chronic loss of the ability of the kidneys to remove waste and concentrate urine without losing electrolytes.

The term "biological sample" as used herein, refers to any substance derived from a living organism. For example, a sample may be derived from blood as a urine sample, serum sample, a plasma sample, and or a whole blood sample. Alternatively, a sample may be derived from a tissue collected, for example, by a biopsy. Such a tissue sample may comprise, for example, kidney tissue, vascular tissue and/or heart tissue. A biological sample may also comprise body fluids including, but not limited to, urine, saliva, or perspiration.

The term "reagent" as used herein, refers to any substance employed to produce a chemical reaction so as to detect, measure, produce, etc., other substances.

DETAILED DESCRIPTION OF THE INVENTION

This invention is related to the field of the prevention and treatment of kidney disease. The treatment of kidney disease may be tailored depending upon the need for, or expectation of, long-term dialysis. For example, prediction of long-term dialysis treatment can be determined by monitoring urine biomarkers related to the development of chronic kidney disease. For example, a normalized time course of hyaluronic acid can be used to determine whether a patient having suffered acute kidney injury will require long-term dialysis.

If research efforts to treat AKI and prevent CKD could be tailored according to long-term prognosis, a more effective clinical strategy could be implemented. In other words, patients predicted to not recover kidney function could be selectively provided aggressive treatment. Conversely, patients with a favorable prognosis would be spared from more aggressive interventions and their potential adverse effects.

I. Kidney Injury and/or Disease

The kidneys are located in the flank (back of the upper abdomen at either side of the spinal column). They are deep within the abdomen and are protected by the spine, lower rib cage, and the strong muscles of the back. This location protects the kidneys from many external forces. They are well-padded for a reason—kidneys are highly vascular organs, which means that they have a large blood supply. If injury occurs, severe bleeding may result.

Kidneys may be injured by damage to the blood vessels that supply or drain them. This may be in the form of aneurysm, arteriovenous fistula, arterial blockage, or renal vein thrombosis. The extent of bleeding depends on the location and the degree of injury. Kidneys may also bleed profusely if they are damaged centrally (on the inside)—this is a life-threatening injury. Fortunately, most kidney injuries caused by blunt trauma occur peripherally, only causing bruising of the kidney (usually a self-limiting process).

People with undiagnosed kidney conditions—such as angiomyolipoma (benign tumor), ureteropelvic junction obstruction (congenital or acquired UPJ Obstruction), and other disorders —are more susceptible to kidney injuries and more likely to have serious complications if they occur. Other causes of kidney injury and bleeding are medical procedures. Kidney biopsies, nephrostomy tube placements, or other surgeries can cause an abnormal connection between an artery and vein (arteriovenous fistula). This is usually a self-limiting problem, but close observation is usually needed. Injury to the kidney can also disrupt the urinary tract, causing leakage of the urine from the kidney.

Each kidney filters about 1700 liters of blood per day and concentrates fluid and waste products into about 1 liter of urine per day. Because of this, the kidneys receive more exposure to toxic substances in the body than almost any other organ. Therefore, they are highly susceptible to injury from toxic substances. Analgesic nephropathy is one of the most common types of toxic damage to the kidney. Exposure to lead, cleaning products, solvents, fuels, or other nephrotoxic chemicals (those which can be toxic to the kidney) can damage kidneys. Excessive buildup of body waste products, such as uric acid (that can occur with gout or with treatment of bone marrow, lymph node, or other disorders) can also damage the kidneys.

Inflammation (irritation with swelling and presence of extra immune cells) caused by immune responses to medications, infection, or other disorders may also injure the structures of the kidney, usually causing various types of glomerulonephritis or acute tubular necrosis (tissue death). Autoimmune disorders may also damage the kidneys. Injury to the kidney may result in short-term damage with minimal or no symptoms. Alternatively, it can be life-threatening because of bleeding and associated shock, or it may result in acute renal failure or chronic renal failure.

Ureteral injuries (injuries to the tubes which carry urine from the kidneys to the bladder) can also be caused by trauma (blunt or penetrating), complications from medical procedures, and other diseases in the retroperitoneum such as retroperitoneal fibrosis (RPF), retroperitoneal sarcomas, or metastatic lymph node positive cancers. Medical therapies (such as OB/GYN surgeries, prior radiation or chemotherapy, and previous abdominopelvic surgeries) increase the risk for ureteral injuries.

A. Acute Kidney Failure

Acute (sudden) kidney failure is the sudden loss of the ability of the kidneys to remove waste and concentrate urine without losing electrolytes. There are many possible causes of kidney damage. They include, but are not limited to, Decreased blood flow, which may occur with extremely low blood pressure caused by trauma, surgery, serious illnesses, septic shock, hemorrhage, burns, or dehydration, Acute tubular necrosis (ATN), Infections that directly injure the kidney such as acute pyelonephritis or septicemia, Urinary tract obstruction (obstructive uropathy), Autoimmune kidney disease such as interstitial nephritis or acute nephritic syndrome, Disorders that cause clotting within the thin blood vessels of the kidney, Idiopathic thrombocytopenic thrombotic purpura (ITTP), Transfusion reaction, Malignant hypertension, Scleroderma, Hemolytic-uremic syndrome, Disorders of childbirth, such as bleeding placenta abruptio or placenta previa Symptoms of acute kidney failure may include, but are not limited to, Decrease in amount of urine (oliguria), Urination stops (anuria), Excessive urination at night, Ankle, feet, and leg swelling, Generalized swelling, fluid retention, Decreased sensation, especially in the hands or feet, Decreased appetite, Metallic taste in mouth, Persistent hiccups, Changes in mental status or mood, Agitation, Drowsiness, Lethargy, Delirium or confusion, Coma, Mood changes, Trouble paying attention, Hallucinations, Slow, sluggish, movements, Seizures, Hand tremor (shaking), Nausea or vomiting, may last for days, Bruising easily, Prolonged bleeding, Nosebleeds, Bloody stools, Flank pain (between the ribs and hips), Fatigue, Breath odor, or High blood pressure.

B. Chronic Kidney Failure

Unlike acute renal failure, chronic renal failure slowly gets worse. It most often results from any disease that causes gradual loss of kidney function. It can range from mild dysfunction to severe kidney failure. The disease may lead to end-stage renal disease (ESRD).

Chronic renal failure usually occurs over a number of years as the internal structures of the kidney are slowly damaged. In the early stages, there may be no symptoms. In fact, progression may be so slow that symptoms do not occur until kidney function is less than one-tenth of normal.

Chronic renal failure and ESRD affect more than 2 out of 1,000 people in the United States. Diabetes and high blood pressure are the two most common causes and account for most cases. Other major causes include, but are not limited to, Alport syndrome, Analgesic nephropathy, Glomerulonephritis of any type (one of the most common causes), Kidney stones and infection, Obstructive uropathy, Polycystic kidney disease, or Reflux nephropathy. Chronic renal failure results in an accumulation of fluid and waste products in the body, leading to a build up of nitrogen waste products in the blood (azotemia) and general ill health. Most body systems are affected by chronic renal failure.

Initial symptoms may include, but are not limited to, Fatigue, Frequent hiccups, General ill feeling, Generalized itching (pruritus), Headache, Nausea, vomiting, or Unintentional weight loss. Further, later symptoms may include, but are not limited to, Blood in the vomit or in stools, Decreased alertness, including drowsiness, confusion, delirium, or coma, Decreased sensation in the hands, feet, or other areas, Easy bruising or bleeding, Increased or decreased urine output, Muscle twitching or cramps, Seizures, or White crystals in and on the skin (uremic frost).

Circulating levels of cytokines and other inflammation markers are markedly elevated in patients with chronic renal failure. This could be caused by increased generation, decreased removal, or both. However, it is not well established to what extent renal function per se contributes to the uremic proinflammatory milieu. Relationships between inflammation and glomerular filtration rate (GFR) were reported in 176 patients (age, 52+/−1 years; GFR, 6.5+/−0.1 mL/min) close to the initiation of renal replacement therapy. Pecoits-Filho et al., Associations between circulating inflammatory markers and residual renal function in CRF patients. Am J Kidney Dis. 2003 June; 41(6):1212-8. For example, circulating levels of high-sensitivity C-reactive protein (hsCRP), tumor necrosis factor-alpha (TNF-alpha), interleukin-6 (IL-6), hyaluronan, and neopterin were measured after an overnight fast. Patients subsequently were subdivided into two groups according to median GFR (6.5 mL/min). Despite the narrow range of GFR (1.8 to 16.5 mL/min), hsCRP, hyaluronan, and neopterin levels were significantly greater in the subgroup with lower GFRs, and significant negative correlations were noted between GFR and IL-6 (rho=−0.18; P<0.05), hyaluronan (rho=−0.25; P<0.001), and neopterin (rho=−0.32; P<0.0005). In a multivariate analysis, age and GFR were associated with inflammation but cardiovascular disease and diabetes mellitus were not. These results show that a low GFR per se is associated with an inflammatory state, suggesting impaired renal elimination of proinflammatory cytokines, increased generation of cytokines in uremia, or an adverse effect of inflammation on renal function.

C. Dialysis

Dialysis (i.e., for example, renal replacement therapy) is a method of removing toxic substances (impurities or wastes) from the blood when the kidneys are unable to do so and can be performed using several different methods. For example, peritoneal dialysis may filter waste by using the peritoneal membrane inside the abdomen. The abdomen is filled with special solutions that help remove toxins. The solutions remain in the abdomen for a time and then are drained out. This form of dialysis can be performed at home, but must be done every day. Alternatively, hemodialysis may be performed by circulating the blood through special filters outside the body. The blood flows across a filter, along with solutions that help remove toxins.

Dialysis uses special ways of accessing the blood in the blood vessels. The access can be temporary or permanent. Temporary access takes the form of dialysis catheters—hollow tubes placed in large veins that can support acceptable blood flows. Most catheters are used in emergency situations for short periods of time. However, catheters called tunneled catheters can be used for prolonged periods of time, often weeks to months. Permanent access is created by surgically joining an artery to a vein. This allows the vein to receive blood at high pressure, leading to a thickening of the vein's wall. This vein can handle repeated puncture and also provides excellent blood flow rates. The connection between an artery and a vein can be made using blood vessels (an arteriovenous fistula, or AVF) or a synthetic bridge (arteriovenous graft, or AVG). Blood is diverted from the access point in the body to a dialysis machine. Here, the blood flows countercurrent to a special solution called the dialysate. The chemical imbalances and impurities of the blood are corrected and the blood is then returned to the body. Typically, most patients undergo hemodialysis for three sessions every week. Each session lasts 3-4 hours. The purpose of dialysis is to assist kidney functions including, filters for the blood, removing waste products, regulating body water, maintaining electrolyte balance, or maintaining blood pH remains between 7.35 and 7.45. Further, dialysis may replace some of the functions for kidneys that aren't working properly that would otherwise result in the death of a patient.

Dialysis is most often used for patients who have kidney failure, but it can also quickly remove drugs or poisons in acute situations. This technique can be life saving in people with acute or chronic kidney failure.

II. Urinary Hyaluronic Acid Biomarker

In one embodiment, the present invention contemplates a urinary hyaluronic acid (HA) biomarker to predict recovery of renal function after acute kidney injury (AKI). In one embodiment, identifying the biomarker provides patient stratification to tailor treatment intensity thereby preventing unnecessary long-term complications.

In one embodiment, the present invention contemplates a method comprising predicting long-term prognosis of AKI early in the disease process. In one embodiment, the method predicts long-term dialysis when urinary HA is persistently elevated between D1-D14 after after initiation of replacement therapy for severe acute kidney injury. In one embodiment, the method predicts long-term dialysis when urinary HA is persistently elevated between D1-D14 after initiation of replacement therapy for severe acute kidney injury. In one embodiment, the long-term dialysis comprises at least sixty (60) days after kidney injury. In one embodiment, the long-term dialysis comprises at least sixty (60) days after kidney disease diagnosis.

The data provided herein was collected from forty-three (43) patients enrolled in a large multicenter randomized controlled trial studying the effect of different RRT doses on AKI survival. In one embodiment, AKI survival was correlated with a urinary hyaluronic acid (HA) biomarker. Although it is not necessary to understand the mechanism of an invention, it is believed that HA (i.e., for example, hyaluronan or hyaluronate) comprises a non-sulfated glycosaminoglycan, and is believed widely distributed throughout connective, epithelial, and neural tissues. HA is also believed to be one of several components within the extracellular matrix and may be involved in tissue repair and remodeling by mediating cell proliferation and migration, synthesis and degradation of extracellular matrix. For example, fragmented HA has been observed to accumulate during tissue injury and may stimulate the expression of inflammatory genes by a variety of immune cells at the injury site. Further, impaired clearance of HA has been seen to result in persistent inflammation.

Figure 5:
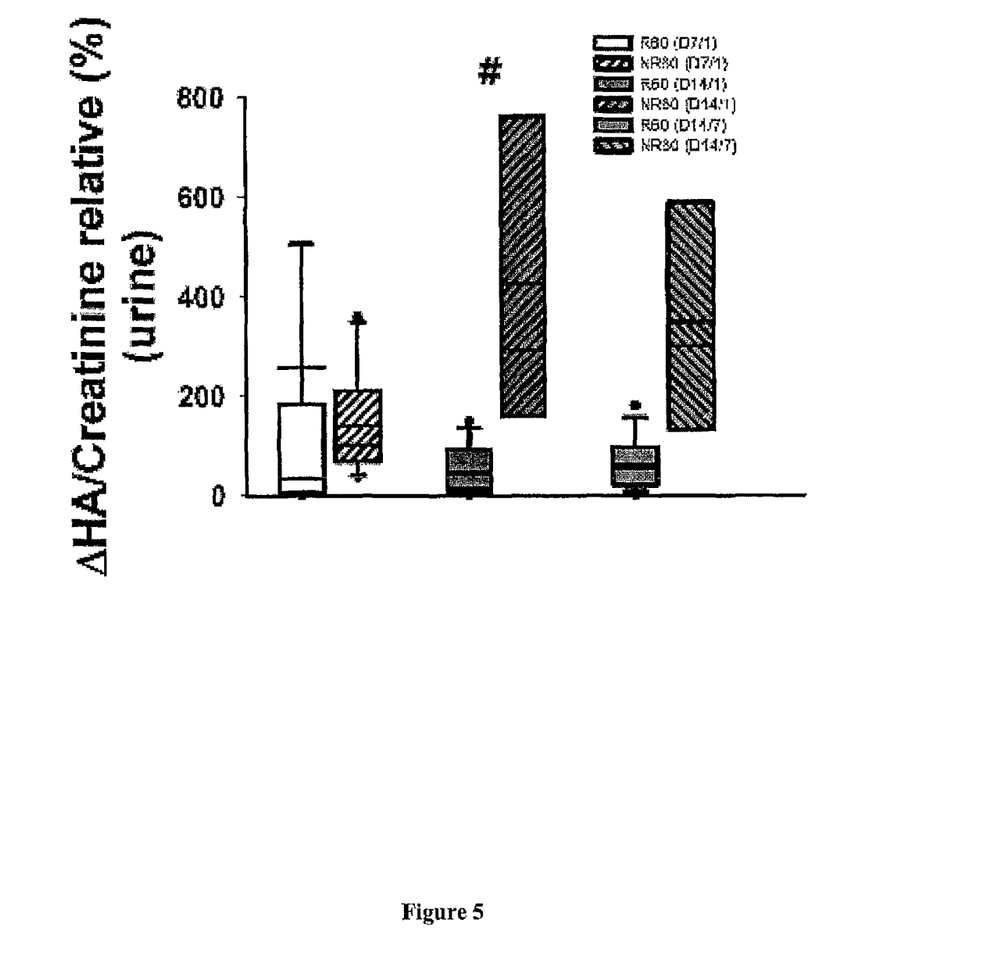
FIG. 5 presents exemplary data showing relative differences between urine samples taken on D1, D7 and/or D14 from patients either recovering or not recovering sixty days after kidney injury (R60 and NR60, respectively).

In one embodiment, the biomarker predicts a non-recovery of renal function, wherein dialysis-dependence is in excess of sixty (60) days. In one embodiment, non-recovery of renal function comprises biomarker elevation above its initial value for at least fourteen (14) days. In one embodiment, the biomarker prediction is supported by a receiver operating characteristic (ROC) analysis. In one embodiment, the ROC analysis provides calculations including, but not limited to, area under fitted curve and/or trapezoidal (Wilcoxon) area. In one embodiment, the area under fitted curve=0.9686 having an estimated standard error=0.0518. In one embodiment, the trapezoidal (Wilcoxon) area=0.9692 having an estimated standard error=0.0568). See, FIG. 5.

A. Hyaluronic Acid

Hyaluronic acid (also known in the art as hyaluronate and hyaluronan, and abbreviated as HA), is a glycosaminoglycan comprising a straight unbranched polysaccharide chain with alternating units of N-acetyl-D-glucosamine and D-glucuronic acid. Laurent T C, Fraser R E. Hyaluronan. FASEB J 1992; 6:2397-2404; and Delpech B, Girard N, Bertrand P. Hyaluronan: fundamental principles and applications in cancer. J Intern Med 1997; 242: 41-48. A is present ubiquitously in various types of biological material, including both bacteria and animals. In humans, HA is found in high concentrations in umbilical cords, vitreous humor of the eyes, cartilage and synovial fluid. Small amounts of HA are present in CSF, lymph, blood, serum and urine. Levels of HA have been associated with diseases such as rheumatoid arthritis, liver cirrhosis, and Wilms' tumor. HA is associated with non-specific tumors in general, but its use has not been applied heretofore to the discovery, therapy and management of particular clinical tumors. HA has been known to play a role in several pathophysiological conditions including cancer.

For example, HA levels have been shown to be elevated in certain animal tumor models (e.g., rabbit V2 carcinoma, Knudson et al., The role and regulation of tumor associated hyaluronan. In: The Biology of Hyaluronan (J. Whelan, ed.), pp. 150-169, New York, Wiley Chichister (Ciba Foundation Symposium 143), 1989) and human cancers (e.g., lung, Wilms' tumor, breast, etc., Knudson et al., ibid.). In tumor tissues, HA supports tumor cell adhesion and migration and also offers some protection against immune surveillance.

Small fragments of HA has also been observed to stimulate angiogenesis, and such fragments are found in the urine of bladder carcinoma patients and tumor tissues. Sattar A, Kumar S, West D C. Does hyaluronan have a role in endothelial cell proliferation of the synovium? Semin Arthritis Rheum 1992; 22:37-43; Lokeshwar V B, Selzer M G. Differences in hyaluronic acid mediated functions and signaling in arterial, microvessel, and vein-derived human endothelial cells. J Biol Chem 2000; 275:27641-27649. Hyaluronic acid fragments are generated when HAase, an endoglycosidase, degrades the HA polymer. Csoka T B, Frost G I, Stern R. Hyaluronidases in tissue invasion. Invasion Metastasis 1997; 17:297-311; and 55. Roden L, Campbell P, Fraser J R, Laurent T C, Petroff H, Thompson J N. Enzymatic pathways of hyaluronan catabolism. In: Whelan J, editor. The Biology of Hyaluronan. New York: Wiley Chichister 1989:60-86. A HA test has been suggested to detect bladder carcinoma, regardless of the tumor grade. Lokeshwar V B, Obek C, Pham H T, Wei D, Young M I, Duncan R C. Urinary hyaluronic acid and hyaluronidase: markers for bladder cancer detection and evaluation of grade. J Urol 2000; 163:348-356.

The efficacy of the HA-HAase test to monitor bladder tumor recurrence as compared to the standard BTA-Stat was recently reported. Lokeshwar et al., Bladder Tumor Markers for Monitoring Recurrence and Screening Comparison of Hyaluronic Acid—Hyaluronidase and BTA-Stat Tests Cancer 95:61-72 (2002). This study suggested that a biochemical test such as the HA-HAase test can detect bladder carcinoma recurrence earlier than cystoscopy. If such early detection can provide a clinical advantage in terms of outcome, cystoscopy may not remain the ultimate gold standard to decide a test's sensitivity, specificity, and accuracy in monitoring recurrence. An interesting corollary to this would be treatment of prostate carcinoma patients and increasing prostate specific antigen after radical prostectomy or radiation therapy the HA-HAase test can be an effective adjunct to cystoscopy for monitoring bladder carcinoma recurrence. With over 90% sensitivity and 86% accuracy, the HA-HAase test can be an effective adjunct to cystoscopy for monitoring bladder carcinoma recurrence. A false-positive HA-HAase test carries a significant risk of recurrence within five months. Thus, it is possible that a combination of biochemical tests can effectively monitor bladder carcinoma recurrence, which may allow a minimum 50% reduction in the number of surveillance cystoscopy procedures.

1. Hyaluronic Acid Assays

Urinary hyaluronic acid may be determined by first collecting voided (clean-catch) urine specimens that are stored at −20° C. until assayed. The HA assay may be based upon an ELISA plate based assay for hyaluronan using biotinylated proteoglycan G1 domain (HA-binding) region. Fosang et al. Matrix, 10:306-313 (1990). In one embodiment, the assay may be modified by using a 96-well microtiter plates coated with human umbilical cord HA (25 µg/ml) that are incubated with serial dilutions of urine specimens in phosphate buffer saline (PBS) +0.05% Tween 20 (PBS+Tween), and a biotinylated bovine nasal cartilage HA-binding protein (1 µg/ml). Following incubation at room temperature for 16 h, the wells were washed in PBS+Tween. The HA binding protein bound to these wells was quantitated using an avidin-biotin detection system and ABTS (2,2'azino-bis(3-ethyl-benzthiazolin-6-sulfonic acid)) substrate (Vector Laboratories, Burlingame, Calif.). A standard graph can be prepared by plotting absorbance (405 nm) versus human umbilical cord HA concentrations (ng/ml). Using this graph, the HA concentration in each dilution of the urine specimen may be calculated. From several such determinations, the mean HA concentration in each sample was determined and then normalized to the creatinine concentration (mg/ml) in the urine sample.

The above described HA assay of the invention has been shown to detest bladder cancer at a sensitivity of about 88% using a cut-off limit of approximately 500 ng/ml. Lokeshwar, et al. Methods for detection and evaluation of bladder cancer U.S. Pat. No. 6,350,571 (herein incorporated by reference). Although it is not necessary to understand the mechanism of an invention, it is believed that cut-off limits of HA concentration may vary, and the population spread must be taken into consideration. Setting the cut-off limit of HA concentration to arrive at appropriate predictors for long-term dialysis may involve considering factors including, but not limited to, age, diet, concentration of protein in the sample, environmental influence, genetic background, hydration status, medical history, physical condition, sex, weight, or the like.

In one embodiment, the HA assay comprises adsorbing HA onto the surface of a solid phase. Although it is not necessary to understand the mechanism of an invention, it is believed that the HA can be derived from any convenient source, such as human umbilical cord. The solid phase can be any conventional solid phase, including nitrocellulose and the like, and preferably microliter wells. After adsorbing HA onto the solid phase, the surface of the solid phase is preferably washed using conventional buffer(s). Because the solid phase still has sites left on its surface which are capable of coupling with the HA or other molecules, it is preferred that prior to addition of the sample a blocking substance be added so as to cover any part of the solid phase on which the HA has not been adsorbed. Examples of suitable blocking substances include γ-globulin and albumin derived from cows or other animals. Bovine serum albumin is preferred. After blocking the free sites of the solid phase, the surface of the solid phase is preferably washed using conventional buffer(s).

Next, HA binding protein (HASP) is added to the coated solid support in the presence of a sample of biological fluid collected from a person suspected of having a kidney injury, and incubated under conditions such that the HABP is permitted to bind to the HA coated on the solid support and the urinary HA (if any is present). The incubation time and conditions can vary within wide limits, but an incubation time of about 4 to about 16 hours, and an incubation temperature of about 4° C. to about 37° C. is satisfactory. Nonetheless, longer or shorter incubation times and higher or lower incubation temperatures are also possible.

HABP suitable for use with the assays of this invention can be readily purified from a number of sources, such as bovine nasal cartilage (Tengblad, Biochim. Biophys. Acta, 578: 281-289, 1979), pig laryngal cartilage (Fosang et al., Matrix, 10: 306-313, 1990). After binding of the HABP to the coated HA and/or the sample HA, the surface of the solid phase is preferably washed using conventional buffer(s). Next, the amount of HABP bound to the HA coated on the solid support is determined. Preferably, the HABP is biotinylated, and the bound HABP is visualized following incubation with an avidin-enzyme conjugate and any substrate for the enzyme which generates a colored product. Such a detection system does not use radioactivity as a label, multiple markers (i.e., enzyme molecules) are immobilized for every HABP bound to the solid support, and the signal (i.e., colored product) is amplified through turnover of the enzyme. However, any conventional marker system may be used in conjunction with the HABP.

Examples of suitable marker systems include enzymes, fluorescence, chemiluminescence, enzyme-substrate, isotope markers, radiolabels and the like. Preferably, the determination of the amount of HABP bound to the HA coated on the solid support is via an avidin-biotin detection system. Another useful marker system employs keratin sulfate and keratin sulfate-reactive antibodies. The urinary HA levels can usefully be determined using a microtiter plate reader, and can be extrapolated from a standard graph. The amount of HABP coupled with the coated HA can then be correlated with the existence of bladder cancer in the patient from whom the sample of biological fluid was collected.

For the HA assay, purified hyaluronic acid is preferably used as a standard.

The HA-binding fragments used in the above assay may be isolated from human umbilical cord HA (.about.500 mg) by digestion with 20,000 units of testicular hyaluronidase (Sigma Chemical Co., St. Louis, Mo.), at 37° C. for different time intervals. The HA fragments generated were separated on a Sephadex G-50 column (1.5×120 cm). Ten ml fractions were collected and assayed for the uronic acid content (Bitter and Muir, A modified uronic acid carbazole reaction. Anal. Biochem., 4:330-334, 1962). The fractions were combined to give three preparations, F1, F2 and F3. The number of reducing ends in each fraction was determined by the Dygert assay (Dygert et al., Determination of reducing sugars with improved precision. Anal. Biochem., 13: 367-374, 1965). Since each linear polysaccharide of HA or its fragment contains a single reducing end, the chain length of each fragment was calculated from the number of reducing ends per mole of uronic acid. The size range of oligosaccharides in each fraction was also determined by incorporating ³H labeled HA (prepared as described in Lokeshwar et al., Ankyrin binding domain of CD44(GP85) is required for the expression of hyaluronic acid-mediated adhesion function. J. Cell Biol., 126 1099-1109, 1994) during HA digestion and analyzing the fragments by gel electrophoresis and fluorography.

Accordingly, in one embodiment of this invention long-term dialysis may be predicted by quantitatively measuring HA in a sample of biological fluid (such as, for instance, a urine specimen) collected from a patient suspected of having a kidney injury and/or disease. Any conventional assay methodology can be used to determine the presence and measurement of HA, including radioassays, sandwich assays, inhibition assays and the like. However, HA is preferably measured a competitive binding assay. More preferably, the assay of the invention works in the same manner as an ELISA test, but does not make use of antibody completing mechanisms.

In one embodiment, long-term dialysis can be predicted using a method, comprising:
  (a) coating a solid support (preferably, microtiter wells) with HA;
  (b) contacting and incubating HA binding protein (HABP) with the coated solid support in the presence of a sample of biological fluid (such as a urine sample) collected from a person suspected of having a kidney injury and/or disease, under conditions such that the HABP is permitted to bind to the HA coated on the solid support and the HA in the sample (if any is present);
  (c) determining the amount of HABP bound to the HA coated on the solid support, and determining therefrom the amount of HA present in the sample.

Although it is not necessary to understand the mechanism of an invention, it is believed that when HA is present in the sample, less HABP will bind to the coated HA, as determined by, for instance, comparison with a standard. In other words, a reduction in the amount HABP bound to the coated HA (i.e., as compared to the controls) would mean elevated HA present in the sample. In one embodiment, elevated urinary HA is predictive of long-term dialysis.

In one embodiment, the method may further comprise detecting a signal associated with, or produced by, the bound HABP. Although it is not necessary to understand the mechanism of an invention, it is believed that the amount of HABP bound to the HA coated on the solid support may be used to determine therefrom the amount of HA present in the sample. For example, a microtiter plate reader can be used to measure absorbance of colored product as an indirect measure of biotinylated HABP bound to the solid support (e.g., an avidin-enzyme conjugate and labeled substrate are used to generate the colored product). The maximum absorbance can be obtained by incubating the HA-coated wells with buffer alone in the absence of any HA or HA-containing sample. A standard graph can then be prepared by plotting absorbance versus ng/well or 0.2 ml of HA. Using this standard graph, the HA concentration (ng/ml) in each dilution of the sample can be calculated. From several such determinations the mean HA concentration in each sample can be determined. Creatinine concentration can be determined such that the HA concentrations can be normalized.

In one embodiment, predicting whether a patient will required long-term dialysis may be determined by the following calculations derived from normalized urinary HA level: HA (ng/ml) extrapolated from a time course graph x dilution factor/mg/ml urinary protein. For example, a low absorbance reading would be indicative of a significant amount of HA in the urine sample, which would itself be indicative of the need for long-term dialysis in the patient.

2. Isolation of HA and HA Fragments from Patient Urine

Urine specimens from normal subjects and patients may be concentrated 10-fold and dialyzed extensively against PBS. Approximately 2 ml of each of the dialyzed specimens (about.20 mg protein) was applied to a Sepharose 6 CL-B column (1.5×120 cm) (Pharmacia, Piscataway, N.J.) equilibrated with PBS. The column was run in PBS at 7 ml/hr and 3.5 ml fractions were collected. The fractions were assayed for HA by the ELISA-like assay as described above. Since the standard globular protein markers and linear polysaccharides such as HA and HA fragments have different shapes, the column was calibrated using human umbilical vein HA (Mr.about.$2\times10^6$ D) and the HA fragments, F1, F2 and F3.

The ELISA-like assay, may involve the use of a biotinylated HA binding protein to determine the HA concentration in urine specimens. Because urinary HA levels (i.e., normally in ng quantities) are found to be influenced by the hydration status and urine output, these levels were normalized to urinary creatinine content.

B. Hyaluronidase

Hyaluronidase (HAase) is an endoglycosidic enzyme that degrades HA by hydrolyzing the N-acetylglucosaminic bonds in HA. The limited degradation of HA by hyaluronidase results in the generation of HA fragments of specific lengths (.about.3-25 disaccharide units) that are angiogenic (West et al., Angiogenesis induced by degradation products of hyaluronic acid. Science, 228: 1324-1326, 1985). In vertebrates, hyaluronidases can be categorized into two classes, those active at neutral pH (pH optimum 5.0), and those active at acidic pH (pH 3.5-4.0) (Roden et al., Enzymatic pathways of hyaluronan catabolism. In: The Biology of hyaluronan, (J. Whelan, ed.), pp. 60-86, New York, Wiley Chichister (Ciba Foundation Symposium 143), 1989; West et al., ibid.; Gold, Purification and properties of hyaluronidase from human liver. Biochem. J., 205: 69-74, 1982; Fraser and Laurent, Turnover and metabolism of Hyaluronan. in: Biology of Hyaluronan, (J. Whelan, ed.), pp. 41-59, New York, Wiley Chichister (Ciba Foundation Symposium 143), 1989; Zhu et al., Molecular cloning of a mammalian hyaluronidase reveals identity with hemopexin, a serum heme-binding protein. J. Biol. Chem., 269: 32092-32097, 1994; Lin et al., A hyaluronidase activity of the sperm plasma membrane protein PH-20 enables sperm to penetrate the cumulus layer surrounding the egg. J. Cell Biol., 125: 1157-1163, 1995). For example, the testicular hyaluronidase is of neutral type whereas the liver hyaluronidase has an acidic pH optimum. The concerted actions of both HA and hyaluronidases are known to play important roles during embryonic development, vasculogenesis, vascular remodeling, immune surveillance and tumor progression (McCormick and Zetter, Adhesive interactions in angiogenesis and metastasis. Pharmacol. Ther., 53: 239-260, 1992; Hobarth et al., Topical chemoprophylaxis of superficial bladder cancer by mitomycin C and adjuvant hyaluronidase, Eur. Urol., 21: 206-210, 1992; Knudson et al., The role and regulation of tumor-associated hyaluronan. In: The Biology of Hyaluronan (J. Whelan, ed.) pp. 150-169, New York, Wiley, Chichester (Ciba Foundation Symposium 143), 1989; Lin et al., Urinary hyaluronic acid is a Wilms' tumor marker. J. Ped. Surg., 30: 304-308, 1995; Stern et al., Hyaluronidase levels in urine from Wilms' tumor patients. J. Natl. Canc. Inst., 83: 1569-1574, 1991).

III. Kits

In one embodiment, the invention contemplates to diagnostic kits for predicting long-term dialysis. In one embodiment, the kit comprises HA and/or HAase, HABP and a marker or HABP conjugated to a marker, and ancillary reagents suitable for use in detecting the presence of HA and/or HAase in a biological sample (i.e., for example, a urine sample). An example of a diagnostic kit contemplated by this invention is a conventional dipstick test device.

In one embodiment, a dipstick test device may support an HA assay to predict long-term dialysis. For example, using conventional methodology a solid phase in the form of a dipstick can be used to assay HA, as described above. In one embodiment, the dipstick can be coated or impregnated with HA, wherein the dipstick may be used to test any biological fluid, including but not limited to urine.

Experimental

EXAMPLE 1

Normalized Hyaluronic Acid in Human Urine Samples

Hyaluronic acid was determined in human urine as described above. A time course was generated by collecting and analyzing HA in urine for two weeks (i.e., fourteen days; D1-D14). The data presented shows recovering patients and non-recovering patients at twenty-eight (28) days after suffering a kidney injury. (i.e., for example, R28=recovering patients; and NR28=non-recovering patients). During the fourteen (14) day collection period samples were analyzed on Day 1 (D1), Day 7(D7), and Day 14 (D14). See, FIG. 1.

Figure 1:
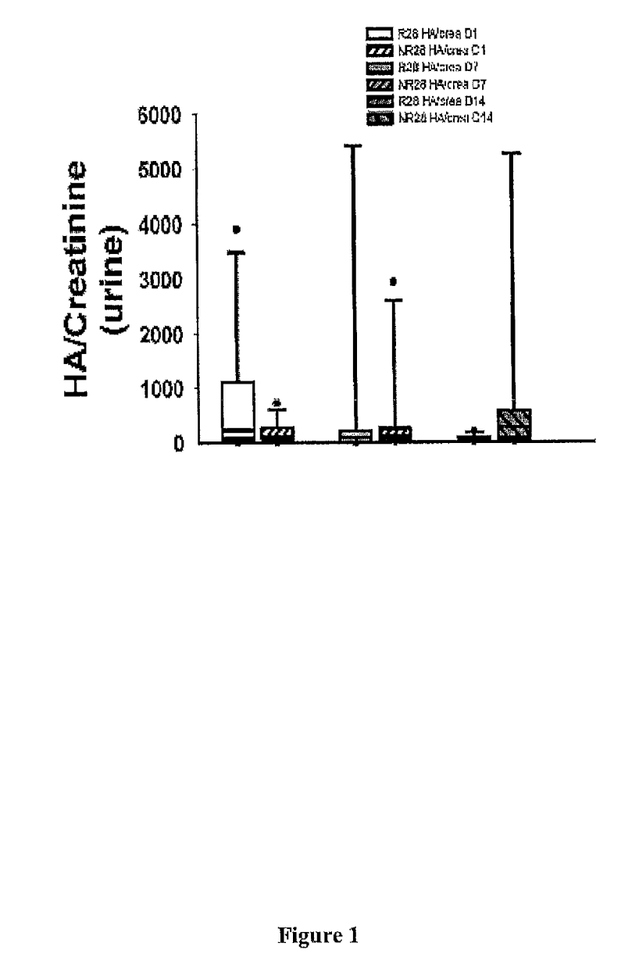
FIG. 1 presents exemplary data showing urine hyaluronic acid excretion normalized to urine creatinine in patients exhibiting acute kidney injury. Samples were taken between one-fourteen days after initiation of replacement therapy for severe acute kidney injury (i.e., D1, D7 and D14). The data shown represent data in patients that were either recovering or not recovering twenty-eight days after kidney injury (R28 and NR28, respectively).

The data demonstrates that for recovering patients, hyaluronic acid was highest on D1 and progressively decreased on D7 and D14. In contrast, for non-recovering patients, hyaluronic acid steadily increased over the same time period. Clearly, the data suggests that hyaluronic acid correlates with recovery from a kidney injury.

EXAMPLE 2

Absolute Normalized Hyaluronic Acid Levels in Human Urine Samples

The data in this example examines the differences between the normalized absolute hyaluronic acid levels above samples taken on D1, D7, and/or D14 after kidney injury collected in accordance with Example 1 for patients showing recovery at both twenty-eight days (R28) and sixty days (R60) past kidney injury, and non-recovering patients (NR28 and NR60).

Figure 2:
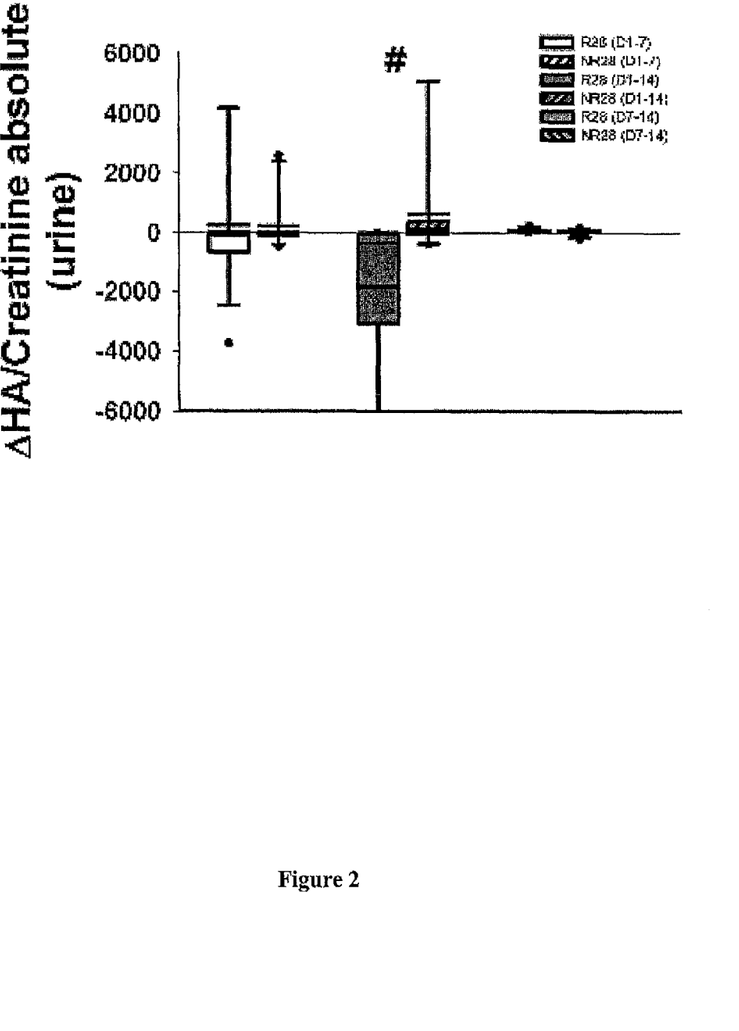
FIG. 2 presents exemplary data showing absolute differences between urine samples taken on D1, D7 and/or D14 from patients either recovering or not recovering twenty-eight days after kidney injury (R28 and NR28, respectively).
Figure 3:
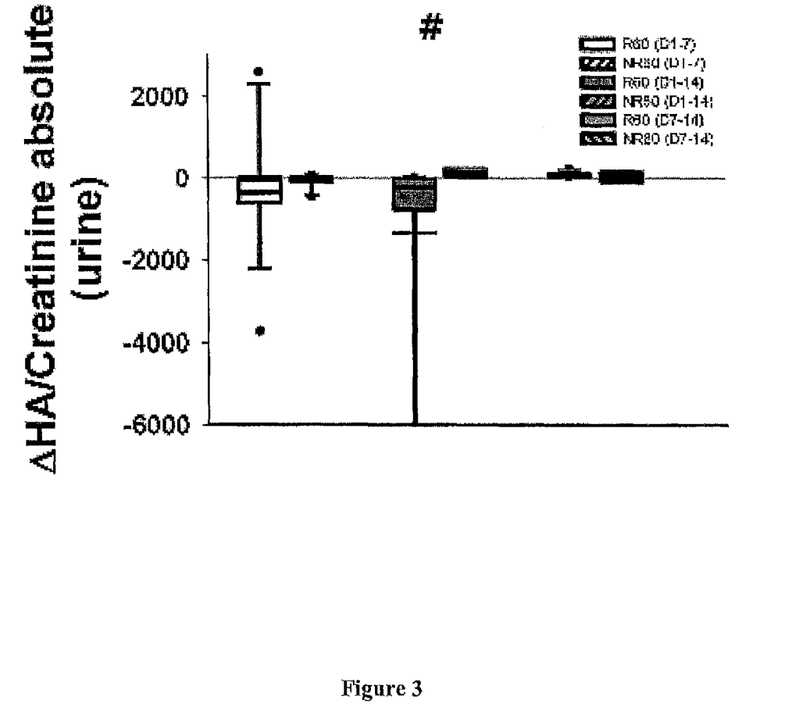
FIG. 3 presents exemplary data showing absolute differences between urine samples taken on D1, D7 and/or D14 from patients either recovering or not recovering sixty days after kidney injury (R60 and NR60, respectively).

The data show that between Day 1 & Day 7, as well as between Day 1 & Day 14, the recovering patients demonstrated clear reductions in excretion of normalized hyaluronic acid (i.e., for example, absolute hyaluronic acid excretion decreased over this time period). The difference between Day 7 & Day 14 was, however, negligible meaning that the excretion rate was unchanged. In contrast, in nonrecovering patients the difference between Day 1 & Day 7, as well as between Day 1 & Day 14 demonstrated clear increases in the excretion of normalized hyaluronic acid (i.e., for example, absolute hyaluronic acid excretion increased over this time period). Also, the excretion rate did not change between Day 7 & 14. See, FIGS. 2 and 3.

EXAMPLE 3

Relative Normalized Hyaluronic Acid Levels in Human Urine Samples

This example replots the data in accordance with Example 2 to further illustrate the magnitude of the differences between recovering patients and non-recovering patients. In particular, the data is expressed as a percentage (i.e., D7÷D1, D14÷D1, D7÷D14, or D14÷D7).

Figure 4:
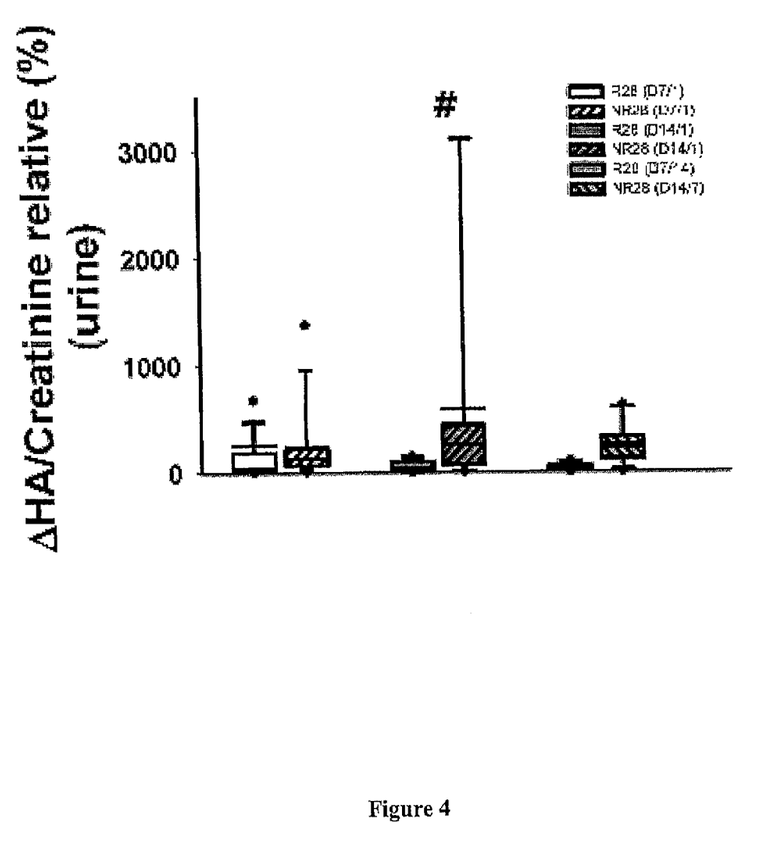
FIG. 4 presents exemplary data showing relative differences between urine samples taken on D1, D7 and/or D14 from patients either recovering or not recovering twenty-eight days after kidney injury (R28 and NR28, respectively).

The data show that in recovering patients that the relative hylauronic acid excretion progressively decreases between Day 1 and Day 14, where the relative difference between Day 14 and Day 7 is almost negligible. This is consistent with the interpretation of the above data suggesting that hyaluronic acid decreases in recovering kidney injury patients over time. In contrast, the data shows that in non-recovering patients the relative hyaluronic acid excretion remained elevated throughout the time period. This is consistent with the interpretation of the above data suggesting that hyaluronic is elevated in non-recovering kidney injury patients over time. See, FIGS. 4 and 5.

EXAMPLE 4

Prediction of Long-Term Dialysis at D14 following Kidney Injury

Figure 6:
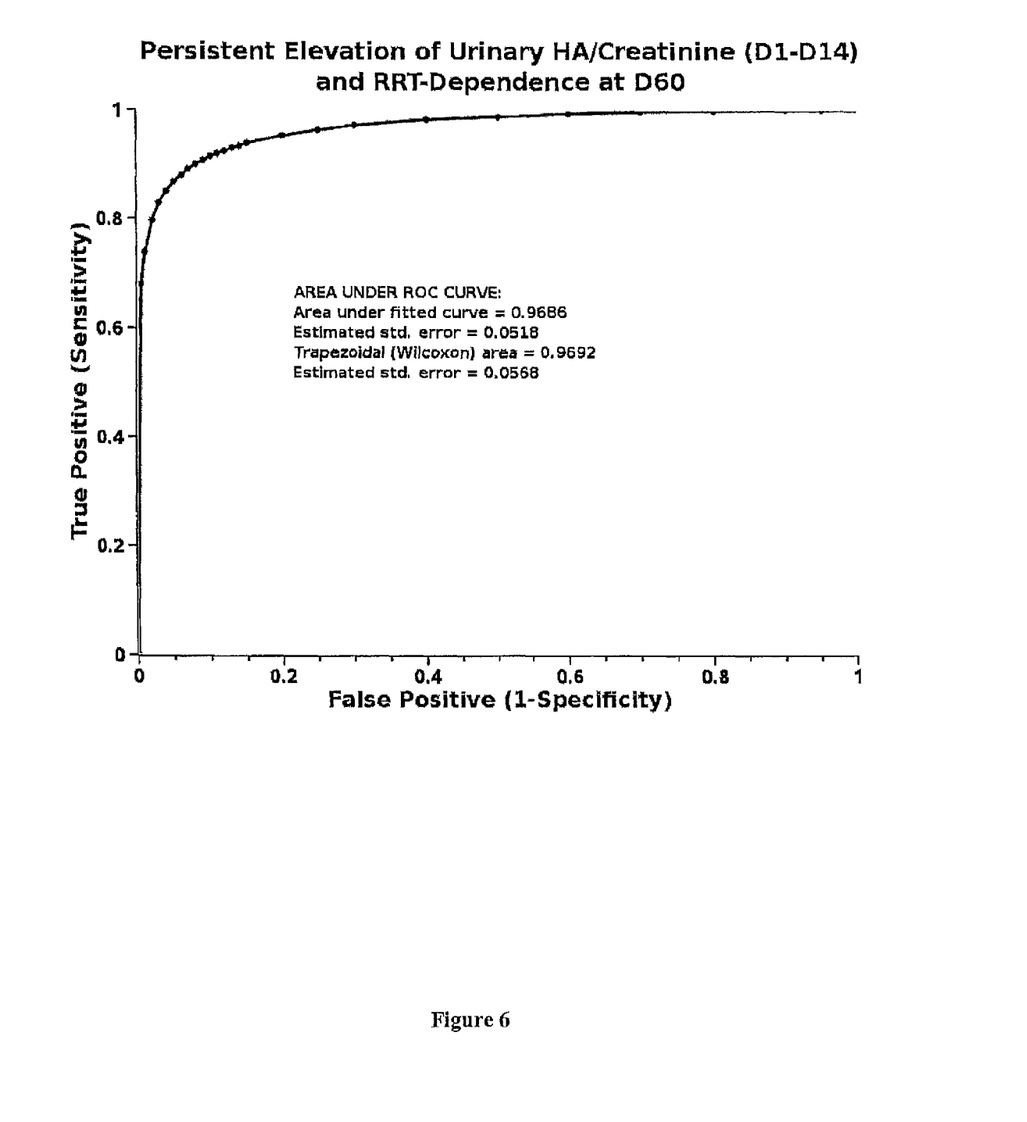
FIG. 6 presents exemplary data showing the high sensitivity of predicting dialysis in patients sixty days after kidney injury, when HA excretion was persistently elevated between D1 and D14.

The data presented in accordance with Example 2 was analyzed and replotted to evaluate the relationship between True Positives and False Positives. In particular, under conditions where there was a persistent elevation of urinary HA/creatinine (i.e., the difference between D1 and D14 measurements) there was a high sensitivity to predicting that the patient would be on long-term dialysis on D60 after kidney injury. See, FIG. 6. In conclusion, the data suggest that in patients demonstrating persistently elevated urinary HA between D1-D14 after kidney injury will be on dialysis on (and most likely after) D60.

We claim:

1. A method, comprising:
a) obtaining at least two urine samples from a patient exhibiting at least one symptom of an acute kidney injury, said patient being asymptomatic for a chronic kidney disease, wherein said at least two urine samples comprise a first sample and a subsequent sample, wherein said first sample is collected within one day of initiation of a renal replacement therapy;
b) contacting each of said at least two urine samples with a solid support comprising a hyaluronic acid marker system;
c) detecting hyaluronic acid in each of said at least two urine samples with a signal generated by said hyaluronic acid marker system; and
d) predicting said patient to require long-term dialysis wherein said hyaluronic acid detected in said subsequent sample is elevated as compared to said hyaluronic acid detected in said first sample within sixty days of said first sample.

2. The method of claim 1, wherein said hyaluronic acid marker system is selected from the group consisting of an enzymatic marker system, a fluorescent marker system, a chemiluminescent marker system, an enzyme-substrate marker system, an isotope marker system and a radiolabel marker system.

3. The method of claim 2, wherein said enzyme-substrate marker system comprises an avidin-biotin marker system.

4. The method of claim 1, wherein said hyaluronic acid marker system comprises a hyaluronic acid binding protein.

5. The method of claim 1, wherein said subsequent sample is collected on the fourteenth day after initiation of said replacement therapy.

6. The method of claim 1, wherein said method further comprises diagnosing said patient with chronic kidney disease.

7. The method of claim 1, wherein said method further comprises entering said patient in a chronic kidney disease prevention program.

8. The method of claim 1, wherein said subsequent sample is collected on the seventh day after initiation of said replacement therapy.

9. The method of claim 1, wherein said first sample is collected on the first day after initiation of said replacement therapy.

* * * * *